United States Patent [19]
Woods et al.

[11] Patent Number: 5,771,524
[45] Date of Patent: Jun. 30, 1998

[54] DISPOSABLE PAD

[75] Inventors: James M. Woods; Marilyn S. Woods, both of Pisgah Forest, N.C.

[73] Assignee: M.J. Woods, Inc., Hendersonville, N.C.

[21] Appl. No.: 775,633

[22] Filed: Dec. 31, 1996

[51] Int. Cl.[6] .................................................. A47K 7/02
[52] U.S. Cl. ................. 15/209.1; 15/229.13; 15/244.1; 602/58; 604/385.1
[58] Field of Search .............................. 15/209.1, 210.1, 15/229.13, 229.14, 244.1, 244.4; 128/155, 851, 888, 917, 849; 132/293, 294; 602/41, 58; 604/289, 310, 358, 365, 367

[56] References Cited

U.S. PATENT DOCUMENTS

| | | |
|---|---|---|
| Re. 26,385 | 5/1968 | Gilchrist . |
| 1,950,840 | 3/1934 | Cook . |
| 1,957,016 | 9/1934 | Nassif . |
| 2,156,270 | 5/1939 | Smith . |
| 2,616,428 | 11/1952 | Magee . |
| 2,629,890 | 3/1953 | Giovanna . |
| 2,653,888 | 9/1953 | Hyman, Jr. . |
| 2,841,811 | 7/1958 | Carroll . |
| 2,927,335 | 3/1960 | Hammond . |
| 2,961,677 | 11/1960 | Zecchini . |
| 2,964,772 | 12/1960 | Crawford . |
| 2,975,453 | 3/1961 | Imhof . |
| 3,104,915 | 9/1963 | Perkovich et al. . |
| 3,131,410 | 5/1964 | Anderson et al. . |
| 3,142,855 | 8/1964 | Gilchrist . |
| 3,221,359 | 12/1965 | Moroni et al. . |
| 3,369,267 | 2/1968 | Friedland et al. . |
| 3,638,270 | 2/1972 | Schlegal, Jr. et al. . |
| 3,666,611 | 5/1972 | Joa . |
| 3,694,845 | 10/1972 | Engelsher . |
| 3,737,939 | 6/1973 | Jones, Sr. . |
| 3,784,998 | 1/1974 | Jones, Sr. . |
| 3,843,991 | 10/1974 | Vallis . |
| 3,955,233 | 5/1976 | Nakamura . |
| 4,014,616 | 3/1977 | Mast, Jr. et al. . |
| 4,053,242 | 10/1977 | Mast, Jr. . |
| 4,121,386 | 10/1978 | Perez . |
| 4,203,857 | 5/1980 | Dugan . |
| 4,342,613 | 8/1982 | O'Leary et al. . |
| 4,372,867 | 2/1983 | Taragos . |
| 4,506,404 | 3/1985 | Clay . |
| 4,562,099 | 12/1985 | Hinchcliffe . |
| 4,684,433 | 8/1987 | Gohr . |
| 4,701,168 | 10/1987 | Gammons . |
| 4,829,995 | 5/1989 | Metters . |
| 4,893,956 | 1/1990 | Wojcik et al. . |
| 4,925,453 | 5/1990 | Kannankeril . |
| 5,230,119 | 7/1993 | Woods et al. . |
| 5,507,906 | 4/1996 | Woods et al. . |

FOREIGN PATENT DOCUMENTS

| | | |
|---|---|---|
| 607525 | 7/1926 | France . |
| 660938 | 7/1929 | France . |
| 5-293070 | 11/1993 | Japan ................................. 15/209.1 |
| 582504 | 12/1976 | Switzerland . |
| 4609 | 3/1915 | United Kingdom . |
| 6160 | 3/1916 | United Kingdom . |
| 1158412 | 7/1969 | United Kingdom . |

*Primary Examiner*—Terrence Till
*Attorney, Agent, or Firm*—Carter & Schnedler, P.A.

[57] ABSTRACT

Multilayer disposable pads for use as wipes or applicators in various applications, including the cosmetics and personal care fields and the medical field. The pads include an absorbent base pad, an impervious barrier layer attached to the base pad, and a flexible handle attached to the barrier layer in a selective attachment area to define a handle attached portion and at least one handle graspable portion. The barrier layer may be attached to the base pad by being coated over the base pad without the use of adhesives, including being fused to the base pad when they are both made of a thermoplastic material. The handle attached portion may be fused to the barrier layer in an ultrasonic bonding process, again without the use of adhesive.

11 Claims, 20 Drawing Sheets

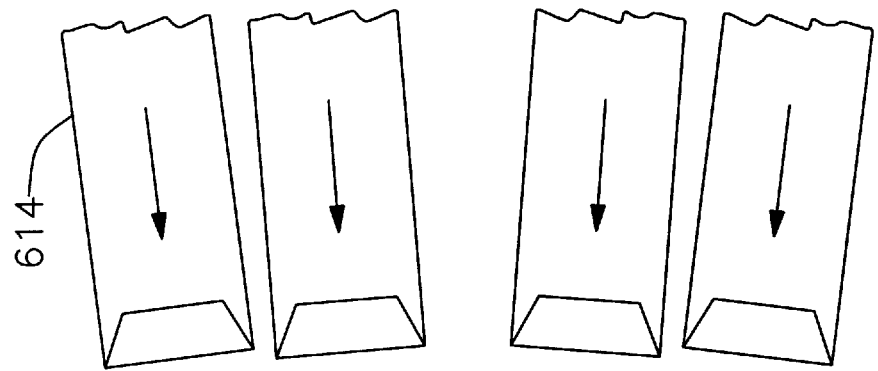
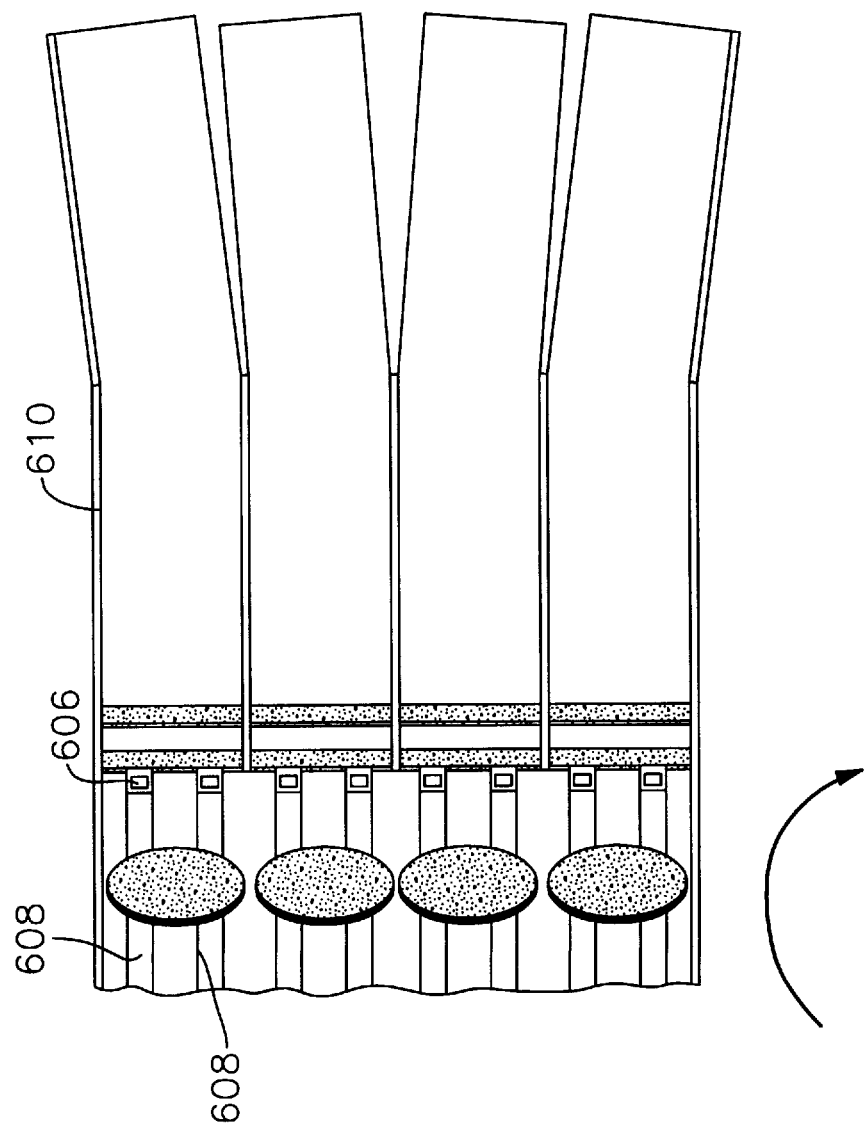
Fig. 32

DISPOSABLE PAD

BACKGROUND OF THE INVENTION

The present invention relates to multilayer disposable pads suitable for use as wipes or applicators in a wide variety of applications, including in the medical and cosmetic fields, as well as methods for making such pads.

Disclosed in Woods et al U.S. Pat. Nos. 5,230,119 and 5,507,906, the entire disclosures of which are hereby expressly incorporated by reference, are various forms of multilayer laminated pads which include between a handle and a base pad an impervious barrier layer that protects the user from contact with fluids and solids on the base pad, and which can be manufactured by machine in large quantities at very low cost.

In the cosmetics and personal care fields, the pads are particularly useful for nail polish removal. The impervious barrier layer avoids finger contact with acetone-and acetate-based nail polish removers, protecting the user's skin from the remover, as well as protecting fingernail polish on the fingernails of the fingers holding the pad. When used for applying and removing make-up, and in applying other personal care products such as lotions, creams, conditioners, astringents and the like, hands-to-skin contact is avoided. This is advantageous when one person is using the pad as an applicator or wipe on himself or herself, as well as in avoiding direct person-to-person contact when one person is using the pad as an applicator or wipe on another person.

In the medical field, the pads are useful in place of traditional cotton balls and gauze. The impervious barrier and absorbent base pad of the multilayer pads allow cleaning, medicating and otherwise preparing the skin for various medical procedures without practitioner-to-patient contact and vice-versa. Contact between the user and substances on the absorbent base pad (blood and other bodily fluids for example) is similarly avoided. As an alternative, the base pad may be manufactured from various dermabrasive and other specialty dermatological materials. The multilayer pads can be pouched or packeted, in single or multiple pads per package. The pads are highly amenable to dispensing.

As disclosed in U.S. Pat. Nos. 5,230,119 and 5,507,906, manufacture of the previously disclosed pads involves initially forming a three-layer laminated sheet by using adhesive to combine base pad material, impervious barrier layer material and handle-producing material. The adhesive which joins the barrier material to the handle-producing material is applied in strips, which may be referred to as "zone coating." A cutter is then used to cut through all three layers of the laminated sheet to produce individual multilayer pads. The cutter is aligned with reference to the adhesive strips securing the handle-producing material to the barrier layer material (and with reference to uncoated areas between the adhesive strips) such that, in each of the resulting pads, one-half of the handle-producing material layer is over an adhesive strip resulting in an adhered segment of the handle, and the other half of the portion of the handle-producing material layer within the shape of the cutter is over an uncoated area to resulting in a free or graspable portion of the handle. The resultant handle lies flat against the barrier layer prior to initial use, and is L-shaped during use.

Efficient mass production is possible, so long as proper alignment of the cutter with reference to the adhesive strips is maintained. Thus, the method ultimately becomes very simple: the three layers are brought together, with continuous adhesive between the base pad layer and the barrier layer, and zoned adhesive strips between the barrier layer and the handle layer. Finished pads are then cut out in a single step. The absorbent base pad, the barrier and the handle have peripheries which are all coextensive since the three layers are cut simultaneously by a single cutter. The zoned adhesive strips in cooperation with the cutter automatically produce a handle with the adhered portion hinged to the graspable portion at the fold line.

The pads and methods previously disclosed nevertheless are subject to improvement. In particular, it is desirable to provide alternative handle structures which are easier to grasp and manipulate. The manufacturing processes can be made even more efficient.

Further, it is desirable to minimize the use of adhesive for securing the various layers together. By using less adhesive, or even eliminating the use of adhesive, significant cost savings can be realized in quantity production. Also, adhesive may be subject to solvent attack, such as by acetone in fingernail polish remover, which could undesirably result in delamination of the pad during use, and adhesives in general are subject to failure. In any event, adhesive application is a process which requires great care. For example, voids in the adhesive are not necessarily evident when the laminated sheet is first produced. However, when the individual pads are cut out, if the cutter is positioned over an unintended adhesive void, a defective pad results.

SUMMARY OF THE INVENTION

Accordingly it is an object of the invention to produce multilayer laminated pads, and to provide corresponding methods of manufacture, in which the use of adhesive is minimized or eliminated.

It is another object of the invention to provide alternative handle structures in multilayer laminated pads, and alternative methods of manufacture.

In accordance with one aspect of the invention, a multilayer pad includes an absorbent base pad having a working side, an opposite side and an outer periphery. An impervious barrier layer has one side joined to the opposite side of the absorbent base pad, preferably in a manner which does not employ an adhesive. For example, the barrier layer may be coated over the base pad, and may actually be fused to the base pad when the barrier layer and base pad are both made of a thermoplastic material.

The multilayer pad additionally has a flexible handle including a central attached portion attached to the other side of the impervious barrier layer in a selective attachment area extending as a strip across the impervious barrier layer, and a pair of graspable portions on either side of the central attached portion. Advantageously the graspable portions are embossed to make them easier to hold between fingers. Where the handle material and barrier layer are of compatible thermoplastic materials, the two may be fused together, employing a process such as ultrasonic bonding. Alternatively, adhesive may be employed.

Prior to initial use, when the graspable portions are lying adjacent to the impervious barrier layer, the base pad, the impervious barrier layer and the handle have coextensive outer peripheries.

In accordance with another aspect of the invention, a multilayer pad includes an absorbent base pad having a working side, an opposite side and an outer periphery. An impervious barrier layer has one side joined to the opposite side of the absorbent base pad, the barrier layer having an outer periphery coextensive with the outer periphery of the absorbent base pad. The impervious barrier layer may be joined to the absorbent base pad by coating barrier layer material over the base pad, and the two may be fused together.

A flexible handle has an attached portion attached to the other side of the impervious barrier layer in a selective attachment area, and at least one graspable portion. The attached portion of the handle may be fused to the impervious barrier layer. The handle has an outer periphery coextensive with the outer peripheries of the absorbent base pad and the impervious barrier layer when the at least graspable portion is lying adjacent to said impervious barrier layer, and the graspable portion is embossed.

In accordance with another aspect, the invention provides a method for manufacturing a plurality of multilayer pads. The method includes the steps of providing a composite material web including a layer of absorbent base pad forming material having a working side and an opposite side, and a layer of impervious barrier forming material coated over to the opposite side of the layer of absorbent base pad forming material. The barrier forming material layer and the base pad forming material layer may be fused together. The composite material web may include a layer of absorbent base pad forming material of non-woven thermoplastic fibers such as polypropylene fibers, and a layer of impervious barrier forming material of thermoplastic material such as polypropylene, formed and fused together by hot extrusion of the impervious barrier forming material over base pad forming material.

A web of handle forming material having an attachment side and an exposed side is provided, and the attachment side of the web of handle forming material is attached to the other side of the layer of barrier forming material in selective attachment areas, such as by employing an adhesive, or fusing by an ultrasonic bonding process.

The method concludes with a step of cutting through the composite material web and the selectively attached web of handle forming material to produce individual multilayer pads, the cutting being related to the selective attachment areas such that each multilayer pad so produced has a handle with an attached portion and at least one graspable portion.

In one form, the handle forming material is attached to the layer of barrier forming material by applying adhesive in strips to define the selective attachment areas as strips, and the cutting is related to the selective attachment areas such that each multilayer pad so produced has a handle with a central attachment portion strip and a pair of graspable portions on either side of the attachment portion strip.

The web of handle forming material may be selectively embossed, prior to the attachment of the handle forming material to the barrier layer, to form embossed areas, separate from the selective attachment areas. The cutting is related to the embossed areas such that the graspable portion is at least partially embossed.

In yet another aspect, the invention provides a method of manufacturing a plurality of multilayer pads, including the steps of providing a web of impervious barrier forming material having first and second sides, providing a web of handle forming material having an attachment side and an exposed side, and fusing the attachment side of the web of handle forming material to the first side of the web of barrier forming material in selective attachment areas, such as by ultrasonic bonding. A web of absorbent base pad forming material is provided, having a working side and an opposite side. The second side of the barrier forming material is adhered to the opposite side of the layer of absorbent base pad forming material, such as by employing an adhesive.

A final step is cutting through the webs to produce individual multilayer pads, the cutting being related to the selective attachment areas such that each multilayer pad so produced has a handle with an attached portion and at least one graspable portion.

In one embodiment, the step of fusing defines the selective attachment areas as strips, and the cutting is related to the selective attachment areas such that each multilayer pad so produced has a handle with a central attachment portion strip and a pair of graspable portions on either side of the attachment portion strip.

The web of handle forming material may be selectively embossed to form embossed areas, separate from the selective attachment areas, and the cutting is related to the embossed areas such that the graspable portion is at least partially embossed.

BRIEF DESCRIPTION OF THE DRAWINGS

While the novel features of the invention are set forth with particularity in the appended claims, the invention, both as to organization and content, will be better understood and appreciated from the following detailed description taken in conjunction with the drawings, in which:

FIG. 32 is a top view of the stacking tubes; and

DETAILED DESCRIPTION

Figure 1:
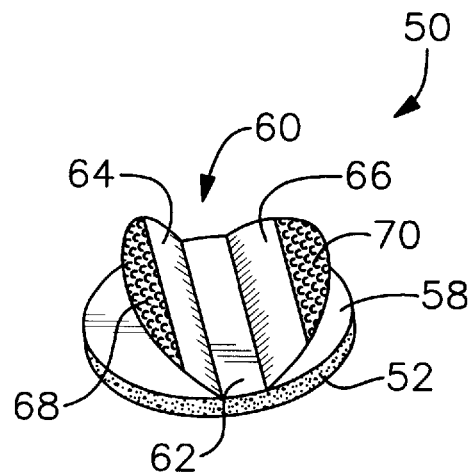
FIG. 1 is a three-dimensional view of a pad in accordance with a first embodiment of the invention.
Figure 2:
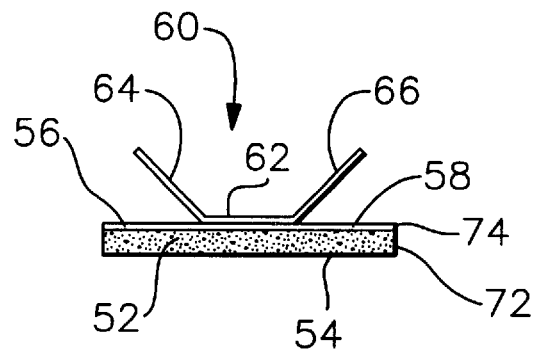
FIG. 2 is a side elevational view of the pad of FIG. 1.

Referring initially to FIGS. 1–5, a multilayer pad 50 includes an absorbent base pad 52 with a working side 54 and an opposite side 56, an impervious barrier layer 58, and a flexible handle 60 having a central attached portion 62 and a pair of graspable portions 64 and 66 on either side of the central attached portion 62. The graspable portions 64 and 66 have respective embossed areas 68 and 70 to aid in grasping. As is perhaps best seen in FIGS. 2 and 5, respective peripheries 72, 74 and 76 of the base pad 52, the barrier layer 58 and the handle 60 are coextensive when the graspable portions 64 and 66 of the handle 60 are lying adjacent to the barrier layer 58 prior to initial use.

A variety of materials may be employed for the base pad 52, which may comprise woven or non-woven fibers, as well as open-or closed-cell foams. The base pad 52 may be made of cotton, or of a thermoplastic such as polypropylene or polyester. Preferably, the base pad 52 is hypo-allergenic. As one example, the base pad 52 may be made of Texel Style No. 235PP 100% polypropylene non-woven material, having a weight of 7.0 oz/sq. yd., and a thickness of 0.110 inch, manufactured by Texel Inc. (Portsmouth N.H. and Quebec, Ontario, Canada.

The barrier layer 58 may comprise a plastic film, or paper coated or impregnated with a plastic such as polyethylene or polypropylene. As one example, the barrier layer 58, as well as the handle 60, may be made of "ADVANTECH 2000 Synthetic paper manufacture by Cosmo," available through Advanced Polymer Associates, Inc. (Medina, Ohio), which is a white opaque oriented polypropylene (BOPP) based synthetic paper, with a smooth, light matte surface on both sides.

Preferably, all three layers, the base pad 52, the barrier layer 58, and the handle 60 are made of a thermoplastic such as polypropylene, which facilitates assembly by various fusing processes, as an alternative to adhesive attachment. Polypropylene as the material from all three layers has the advantage that it can be recycled. Individual pads 52 can be recycled as well as scrap material left over after cutting during the manufacturing process.

Figure 3:
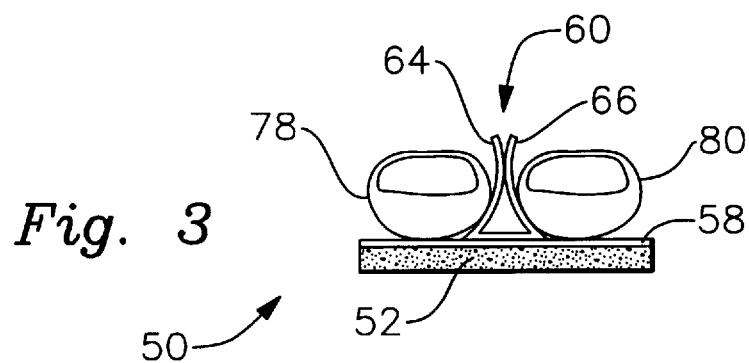
FIG. 3 is a view in the same orientation as FIG. 2, depicting one way in which the pad of FIG. 1 may be grasped.
Figure 4:
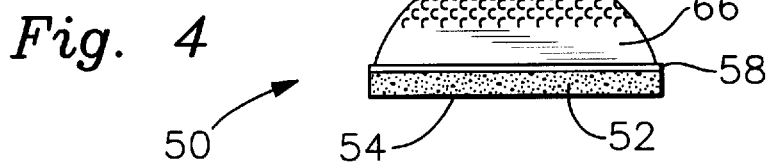
FIG. 4, is another side elevational view, oriented at right angles with reference to the views of FIGS. 2 and 3.
Figure 5:
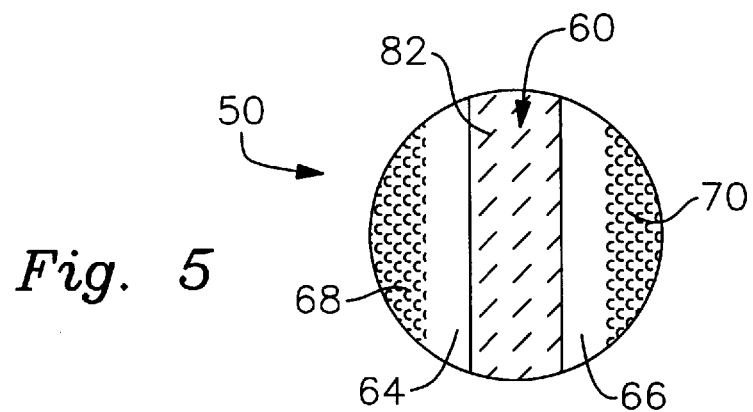
FIG. 5 is a top plan view of the pad of FIG. 1, with the graspable portions of the handle lying adjacent to the barrier layer.

FIG. 3 depicts one manner in which the multilayer pad 50 may be grasped by the handle 60 graspable portions 64 and 66, aided by finger 78, 80 engagement with the embossed areas 68 and 70 (not evident in FIG. 3). Alternatively, the pad 50 may be grasped in employing three fingers (not shown), one in the middle between the two graspable portions 64 and 66, and the other two fingers on the outer sides, similar to the position of the fingers 78 and 80 in FIG. 3.

The various layers of the pad 50 may be assembled together employing a variety of methods and attachment sequences. In one form, the barrier layer 58 is coated over the absorbent base pad 52 employing a process commonly employed to waterproof various fabrics for clothing and another purposes. In a general coating process, barrier layer 58 coating material partially penetrates an upper sublayer of the absorbent base pad 52. In cases where the barrier layer 58 and absorbent base pad 52 are of compatible thermoplastic material, such as both being made of polypropylene, the barrier layer 58 is fused to the absorbent base pad 52 by hot extrusion of barrier layer 58 material over absorbent base pad material 52.

Alternatively, the barrier layer 58 may be adhesively attached to the base pad 52, employing a suitable hot-melt, solvent-based or water-based adhesive.

One side of the barrier layer 58 is uniformly joined to the opposite side 56 of the absorbent base pad 52. The central attached portion 62 of the handle 60 is joined to the other side of the impervious barrier layer 58 in a selective attachment area 82 extending as a strip across the barrier layer 58, as is shown in dash lines in FIG. 5. (The selective attachment area 82 is actually hidden from view in the orientation of FIG. 5.)

Figure 6:
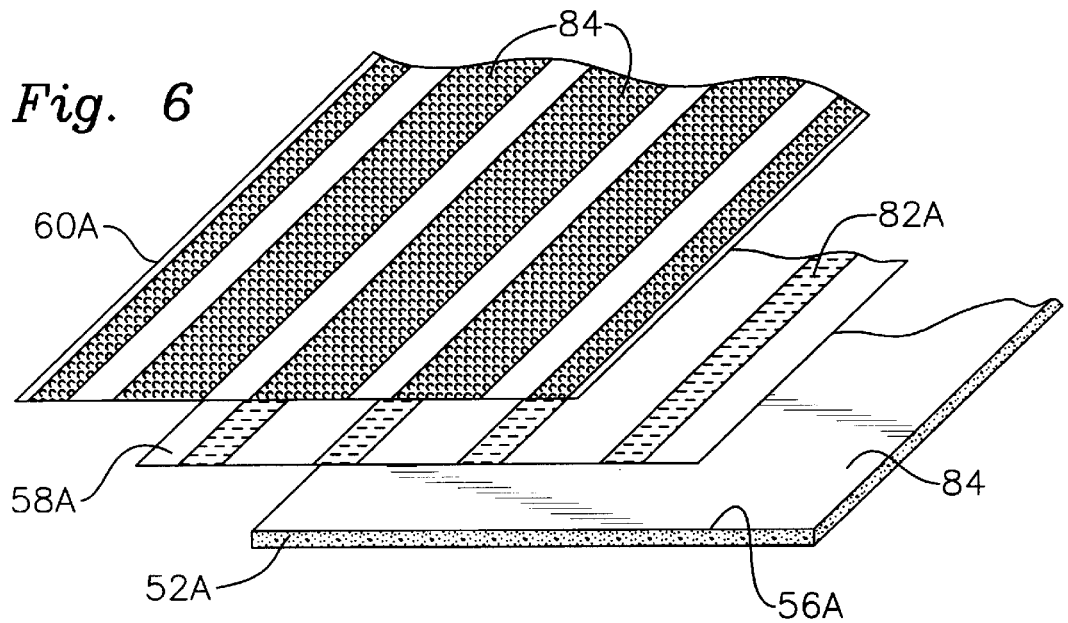
FIG. 6 schematically depicts part of a manufacturing process for making a plurality of pads like the pad of FIG. 1.

With reference to FIG. 6, a part of a representative process is a conceptually illustrated, wherein a web 52A of base pad forming material, a web 58A of barrier layer forming material, and a web 60A of handle forming material are in a position to be laminated together.

In FIG. 6, the opposite side 56A of the base pad forming material 52A is uniformly coated with adhesive 84, and the top of the barrier layer forming material 58A in the FIG. 6 orientation is coated with adhesive in strips 82A to define the selective attachment areas 82. The web 60A of handle forming material has embossed areas 84, which, after cutting, become the embossed areas 68 and 70 of the pad 50.

Figure 7:
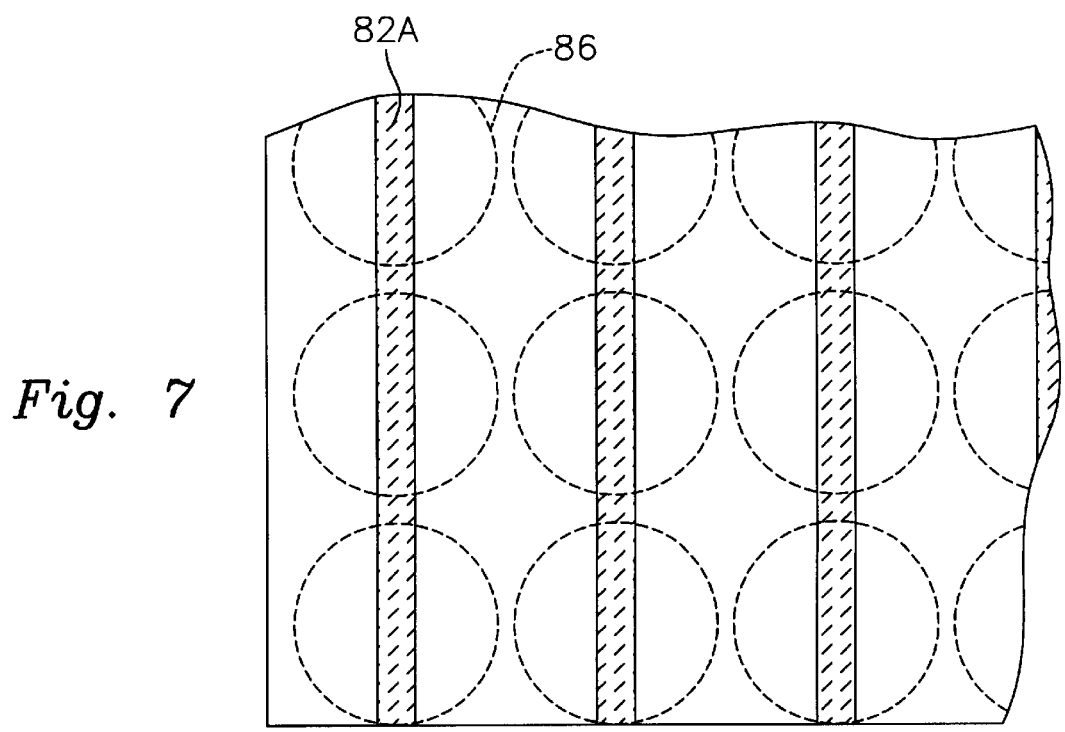
FIG. 7 schematically depicts another part of the manufacturing process.

FIG. 7 is a conceptual plan view showing the relationship of future die-cut lines 86 to the selective attachment areas 82 defined by the adhesive strips 82A, which results in the FIG. 1 pad configuration 50 when individual pads are cut out.

Figure 8:
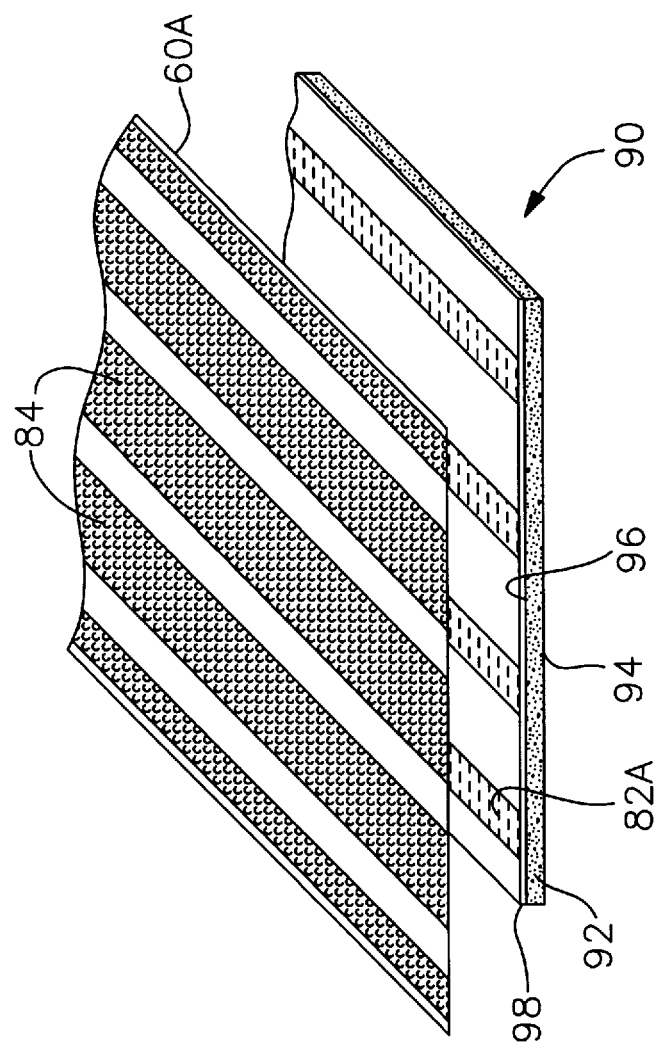
FIG. 8 schematically depicts a variation of the manufacturing process.
Figure 9:
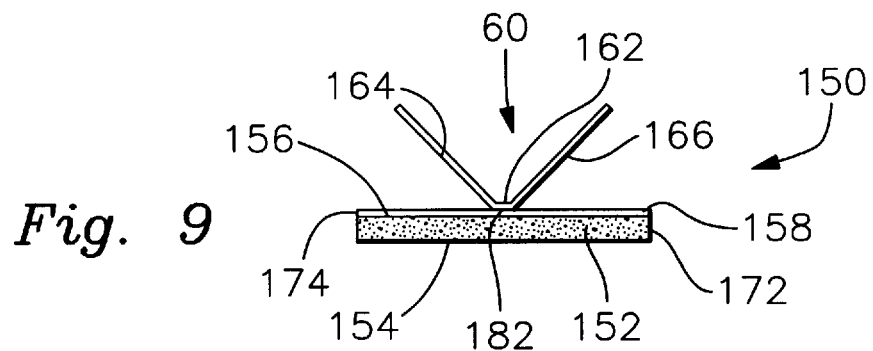
FIG. 9 is a side elevational view, in the same orientation of FIG. 2, depicting a second multilayer pad embodiment.
Figure 10:
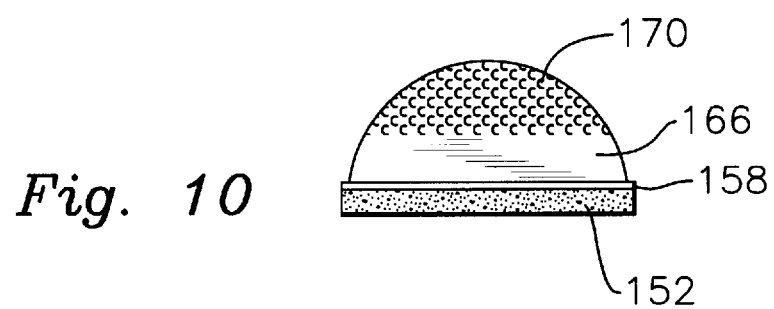
FIG. 10 is another side elevational view of the pad of FIG. 9, oriented generally at right angles to the view of FIG. 9.
Figure 11:
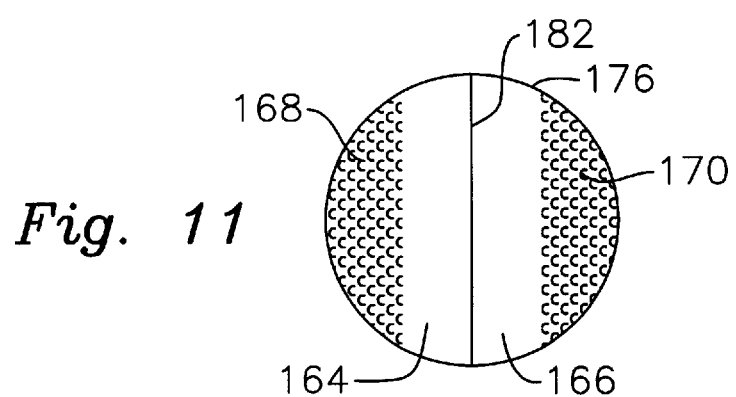
FIG. 11 is a top plan view of the pad of FIG. 9.

FIG. 8 is a highly schematic representation of a variation of the overall process, wherein a composite material web 90 includes a layer 92 of absorbent base pad forming material having a working side 94 and an opposite side 96, and a layer 98 of impervious barrier forming material coated over the opposite side 96 of the layer 92 of absorbent base pad forming material. Material as a precursor to the layer 98 of impervious barrier layer forming material is coated over the layer 92 of absorbent base pad forming material employing a process commonly employed to waterproof various fabric for clothing and other purposes. In a general coating process, barrier layer forming material 98 partially penetrates an upper sublayer of the layer 92 of absorbent base pad forming material. If the layer 98 of barrier layer forming material and the layer 92 of base pad forming material are of compatible thermoplastic materials, such as both being made of polypropylene, the layer 98 of barrier layer forming material is fused to the layer 92 of base pad forming material by hot extrusion of material forming the layer 98 of barrier layer forming material over the layer 92 of base pad forming material.

As one example, such processes are employed by Beckwith Bemis, Inc. (Marshfield, Mass.) to extrusion coat a two mil polypropylene film over fabric.

The layer of handle-forming material 60A is positioned over the web 90, as in FIG. 6, and adhesive strips 82A define selective attachment areas.

In addition to the avoiding the use of adhesive to attach the barrier layer 58 to the base pad 52, the coated barrier 58 has a slight surface texture compared to the smooth surface of a separate plastic film barrier layer 58, such that the handle 60 graspable portions 64 and 66 tend not to stick as much to the barrier layer, making them easier to lift up and grasp. This effect is aided by the embossed areas 68 and 70, which also aid in identifying the graspable portions 64 and 66 to the user.

Referring next to FIGS. 9–13, depicted is a second multilayer pad embodiment 150, and highly schematic representations of a process for making. Like the pad 50 of FIGS. 1–5, the multilayer pad 150 of FIGS. 9–11 includes an absorbent base pad 152 with a working side 154 and an opposite side 156, an impervious barrier layer 158, and a flexible handle 160 having a central attached portion 162 and a pair of graspable portions 164 and 166 on either side of the central attached portion 162. The graspable portions 164 and 166 have respective embossed areas 168 and 170 to aid in grasping. Respective peripheries 172, 174 and 176 of the base pad 152, the barrier layer 158 and the handle 160 are coextensive when the graspable portions 164 and 166 of the handle 160 are lying adjacent to the barrier layer 158 prior to initial use.

One side of the barrier layer 158 is uniformly joined to the opposite side 156 of the absorbent base pad 152. The central attached portion 162 of the handle 160 is joined to the other side of the impervious barrier layer 198 in a selective attachment area 182 extending as a line across the barrier layer 158, as is shown in dash lines in FIG. 11. The selective attachment area 182 is formed by ultrasonic bonding, which fuses the materials together.

Figure 12:
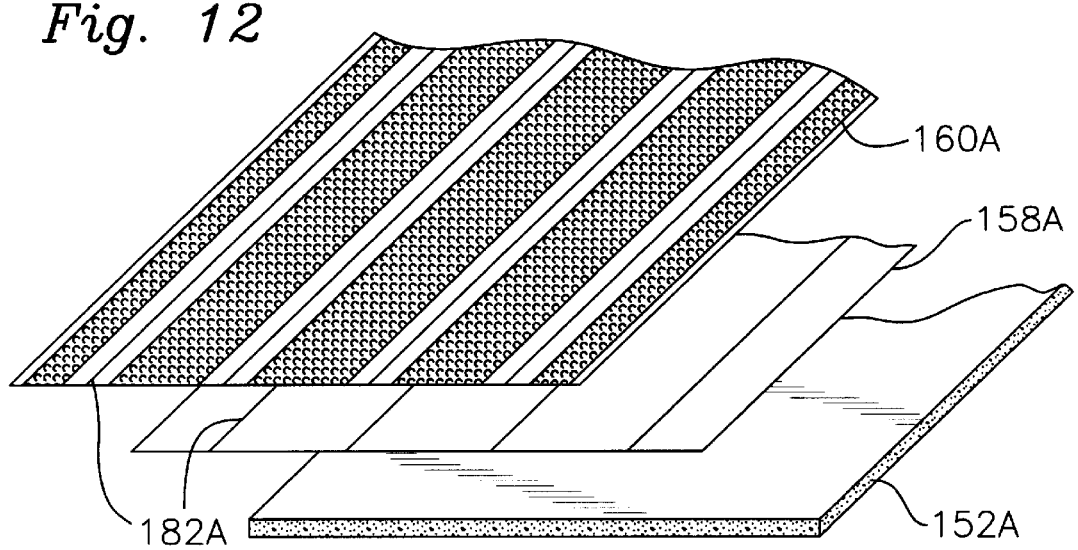
FIG. 12 schematically depicts part of a manufacturing process for making a plurality of pads like the pad of FIG. 9.

In a process for manufacturing, and with reference to FIG. 12, the barrier layer forming material 158A is bonded to the handle forming material 160A first, along ultrasonic bond lines 182A, and then the barrier and handle layers 158A and 160A are attached to the base pad forming material layer 152A, by means of a full adhesive coating.

Figure 13:
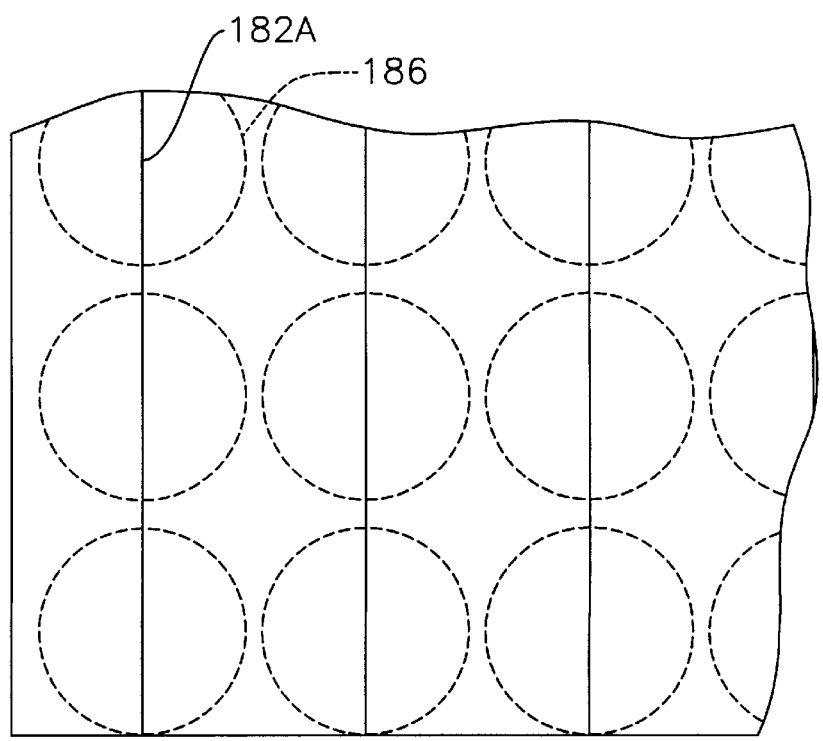
FIG. 13 schematically depicts another part of the manufacturing process.
Figure 14:
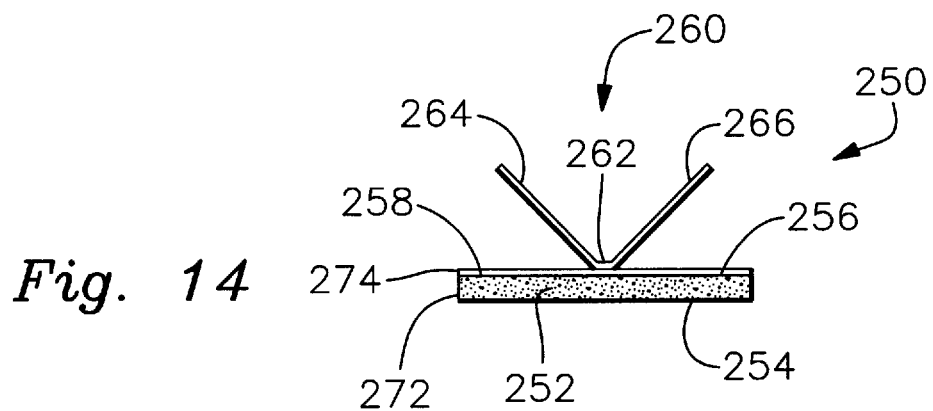
FIG. 14 is a side elevational view of yet another pad embodiment.
Figure 15:
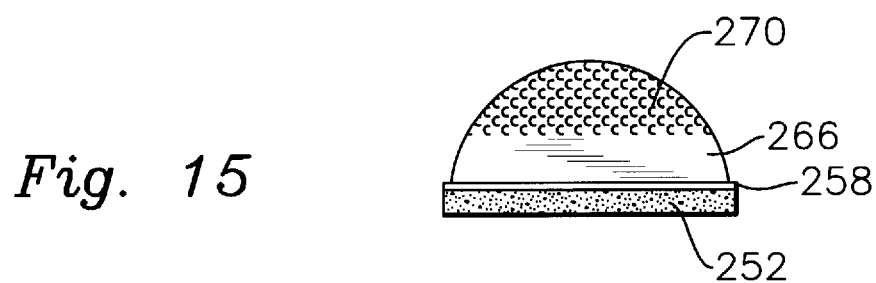
FIG. 15 is a side elevational view of the pad of FIG. 14, oriented at right angles to the view of FIG. 14.
Figure 16:
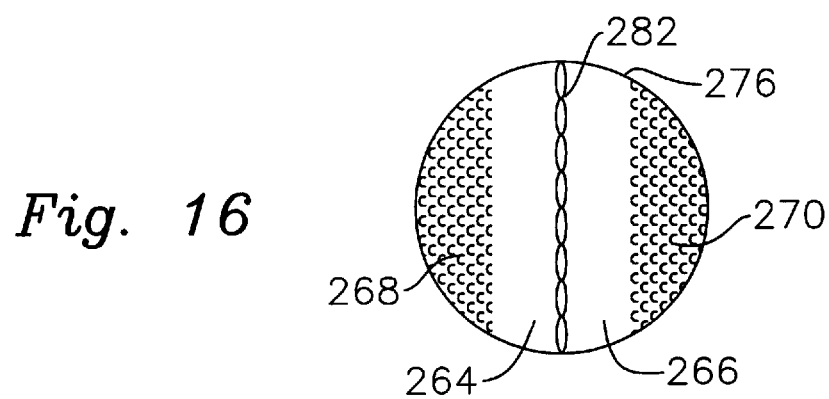
FIG. 16 is a top plan view of the pad of FIG. 14.

FIG. 13 is a view comparable to FIG. 7, showing the manner in which future die cut lines 186 are related to the ultrasonic bond lines 182A, defining selective attachment areas.

FIGS. 14–18 depict a third multilayer pad embodiment 250, and highly schematic representations of a process for making, wherein ultrasonic stitching, rather than ultrasonic bonding in a line is employed. Like the pad 50 of FIGS. 1–5, the multilayer pad 250 of FIGS. 14–16 includes an absorbent base pad 252 with a working side 254 and an opposite side 256, an impervious barrier layer 258, and a flexible handle 260 having a central attached portion 262 and a pair of graspable portions 264 and 266 on either side of the central attached portion 262. The graspable portions 264 and 266 have respective embossed areas 268 and 270 to aid in grasping. Respective peripheries 272, 274 and 276 of the base pad 252, the barrier layer 258 and the handle 260 are coextensive when the graspable portions 264 and 266 of the handle 260 are lying adjacent to the barrier layer 258 prior to initial use.

One side of the barrier layer 258 is uniformly joined to the opposite side 256 of the absorbent base pad 252. The central attached portion 262 of the handle 260 is joined to the other side of the impervious barrier layer 258 in a selective attachment area 282 extending as a series of ultrasonic stitches across the barrier layer 258, as is shown in dash lines in FIG. 11. The selective attachment area 282 is formed by ultrasonic stitching, which fuses the materials together.

Figure 17:
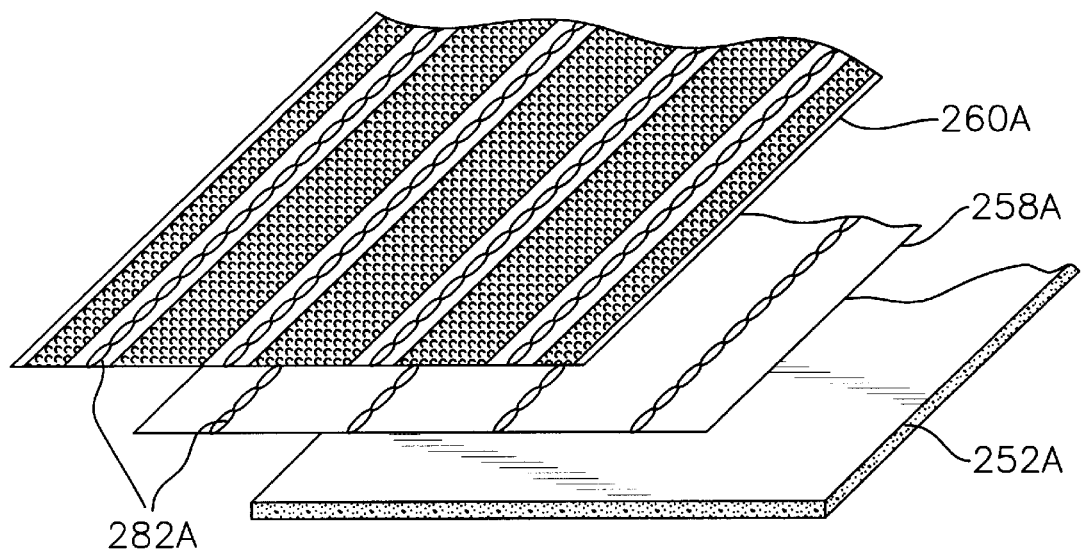
FIG. 17 schematically illustrates part of a process for making a plurality of pads like the pad of FIG. 14.

In a process for manufacturing, and with reference to FIG. 17, the barrier layer forming material 258A is bonded to the handle forming material 260A first, along ultrasonic stitching lines 282A, and then the barrier and handle layers 258A and 260A are attached to the base pad forming material layer 252A, by means of a full adhesive coating.

Figure 18:
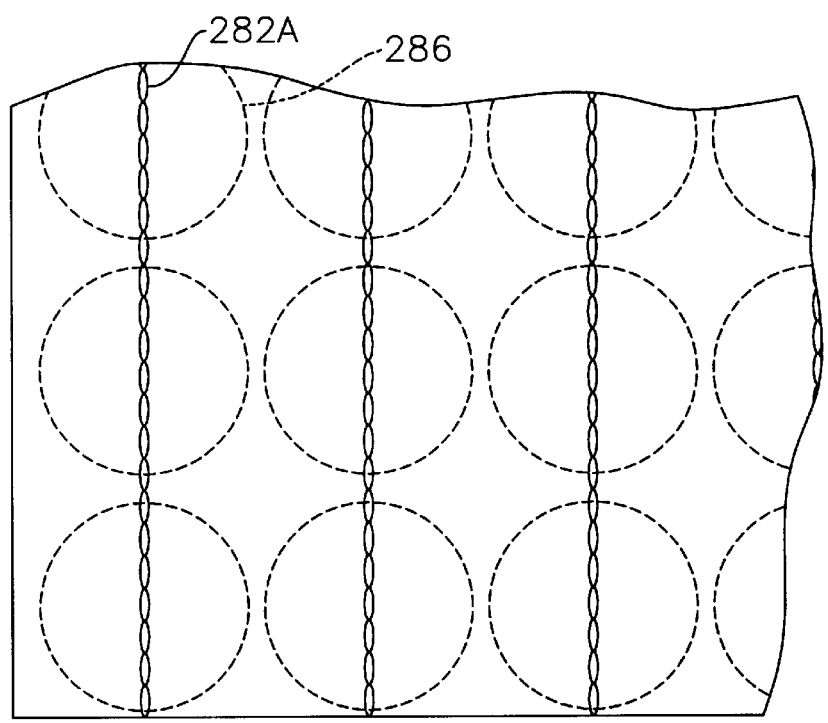
FIG. 18 schematically depicts another part of the manufacturing process.
Figure 19:
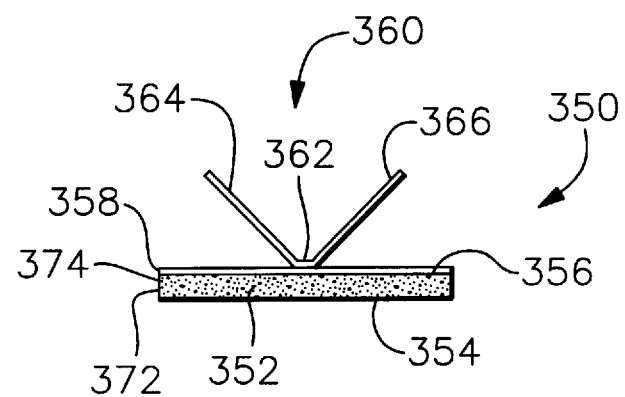
FIG. 19 is a side elevational view of yet another pad embodiment of the invention.
Figure 20:
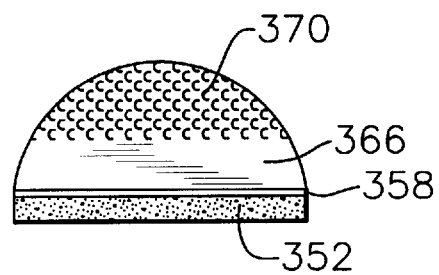
FIG. 20 is a side elevational view of the pad of FIG. 19, taken at right angles to the orientation of FIG. 19.
Figure 21:
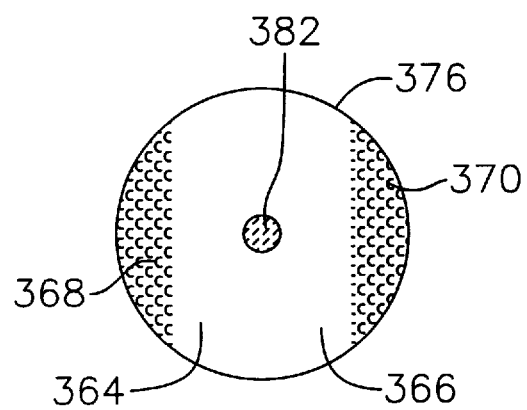
FIG. 21 is a top plan view of the pad of FIG. 19.

FIG. 18 is a view comparable to FIG. 7, showing the manner in which future die cut lines 286 are related to the ultrasonic bond lines 282A, defining selective attachment areas.

FIGS. 19–23 depict a fourth multilayer pad embodiment 350, and highly schematic representations of a process for making, wherein the handle 356 and barrier 354 are selectively attached at the center of each pad 350. Like the pad 50 of FIGS. 1–5, the multilayer pad 350 of FIGS. 19–21 includes an absorbent base pad 352 with a working side 354 and an opposite side 356, an impervious barrier layer 358, and a flexible handle 360 having a central attached portion 362 and a pair of graspable portions 364 and 366 on either side of the central attached portion 362. The graspable portions 364 and 366 have respective embossed areas 368 and 370 to aid in grasping. Respective peripheries 372, 374 and 376 of the base pad 352, the barrier layer 358 and the handle 360 are coextensive when the graspable portions 364 and 366 of the handle 360 are lying adjacent to the barrier layer 358 prior to initial use.

One side of the barrier layer 358 is uniformly joined to the opposite side 356 of the absorbent base pad 352. The central attached portion 362 of the handle 360 is joined to the other side of the impervious barrier layer 158 in a selective attachment area 382, comprising an ultrasonically bonded central circle or dot. The embodiment 350 may be manufactured in several ways.

Figure 22:
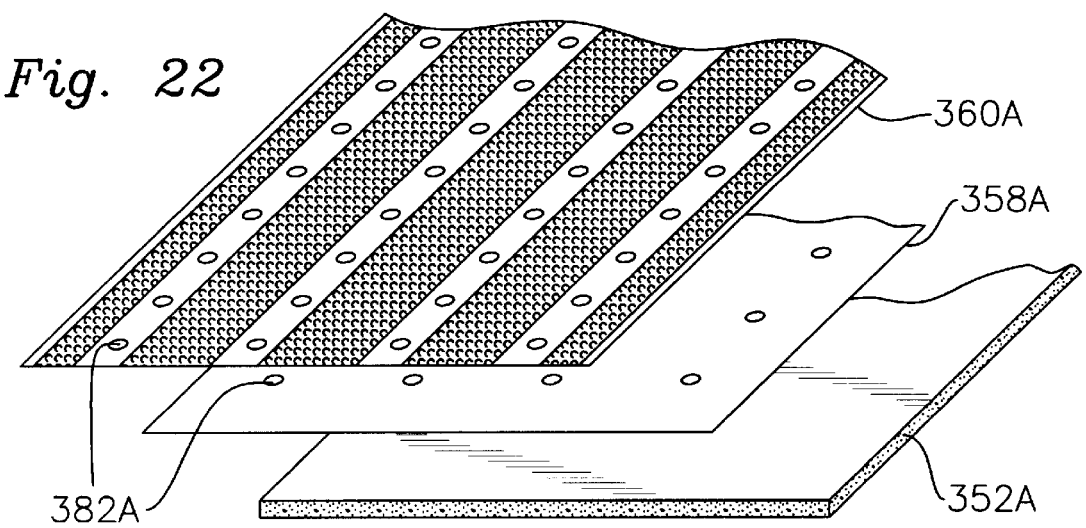
FIG. 22 schematically represents part of a manufacturing process for making a plurality of pads like the pad of FIG. 19.
Figure 23:
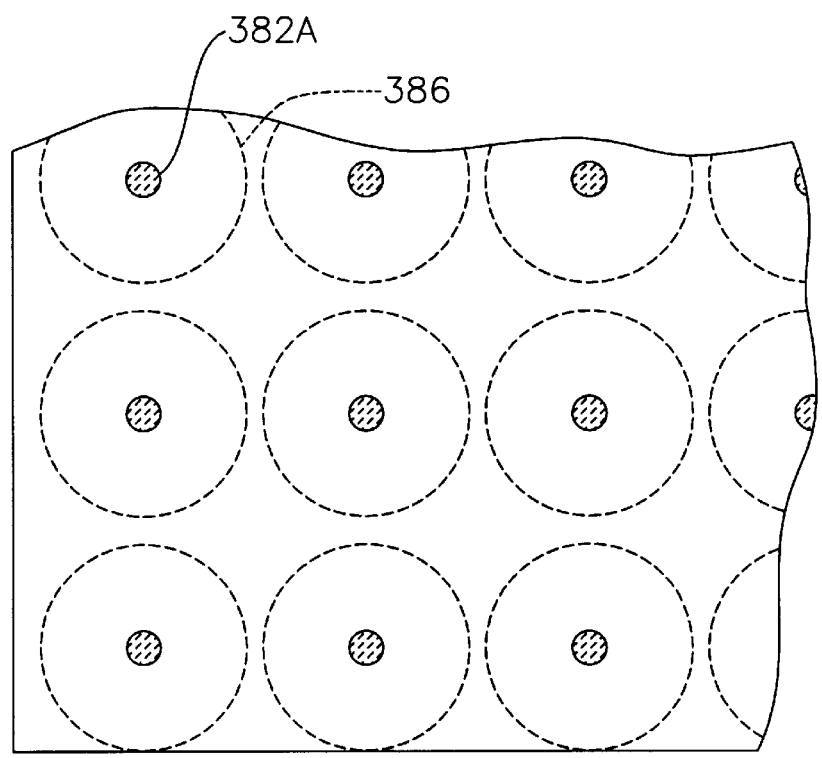
FIG. 23 schematically depicts another part of the manufacturing process.

As represented in FIG. 22, and corresponding to the processes of FIGS. 12 and 17, the barrier forming layer 258A and handle forming layer 360A are first selectively attached to each other in locations 382A which ultimately become the center of each pad, as depicted in FIG. 23, and the two layers 358A and 360A are then together adhesively bonded to the base pad forming material 352A. Future die cut lines 386 are also shown in FIG. 23.

Alternatively, the barrier forming layer 358A and the base pad forming material 356A may be formed by extruding the barrier layer 358A over the base pad layer 352A, as described hereinabove with reference to FIG. 8, and then selectively attaching the handle forming layer 360A in selective attachment areas 382 at the center of each pad 350, preferably employing ultrasonic bonding, applying the ultrasonic bonding tool to the top and bottom of the structure. The central selective attachment areas 382 can have any suitable shape, such as a small circle or dot, or a small square. While such process may result in localized deformation of the pad-forming material 352A, this process advantageously totally eliminates the use of adhesive.

Figure 24:
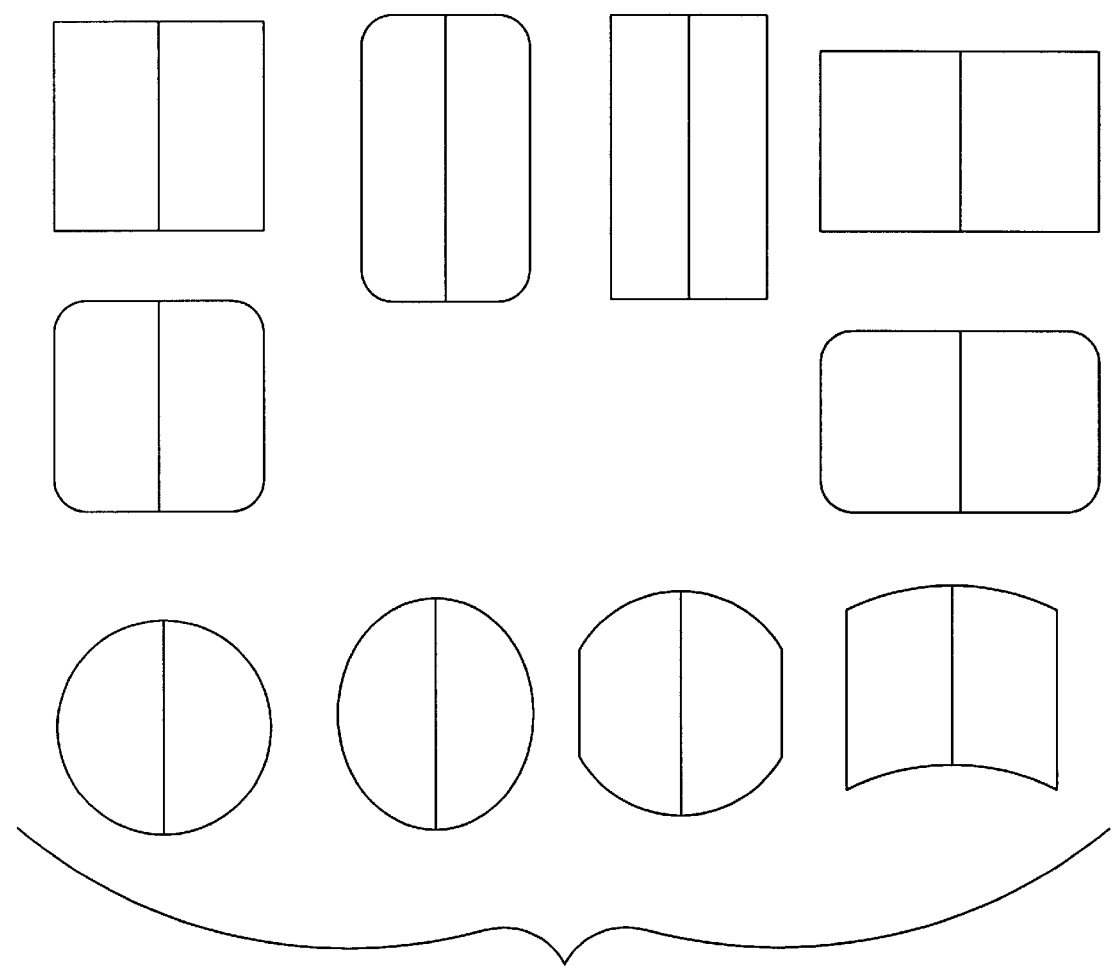
FIG. 24 shows representations of various shapes of multilayer pads which may be produced in accordance with the invention.

FIG. 24 represents a variety of pad shapes which may be employed for various applications. It will be appreciated that some of these shapes result in less material wastage than others.

Figure 25:
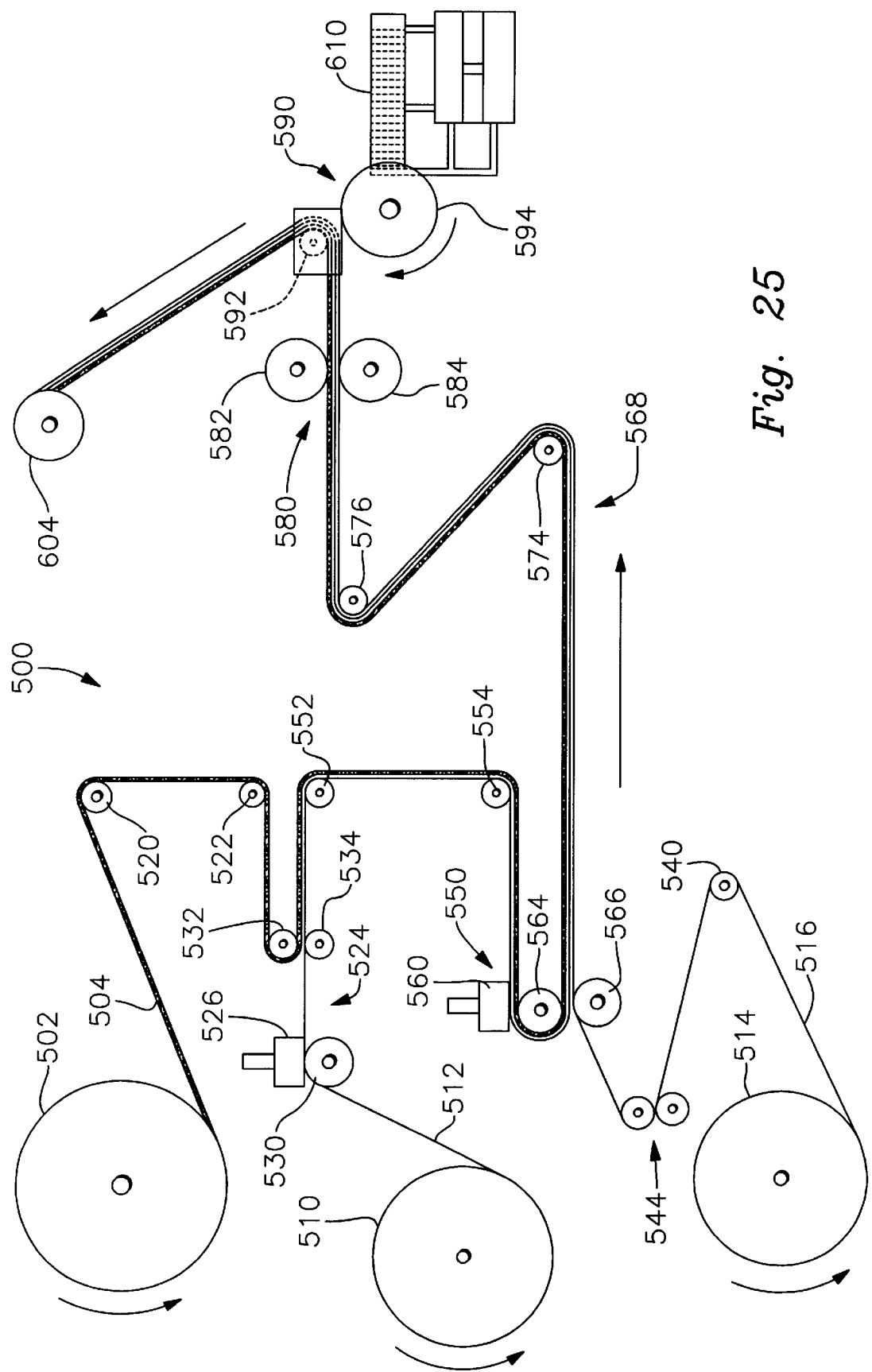
FIG. 25 is a schematic overview of a machine for producing multilayer pads in accordance with the invention.

With reference to FIG. 25, schematically depicted in overview is one embodiment of a machine 500 for manufacturing multilayer pads in accordance with the invention. The machine 500 includes a first supply roll 502 supplying a web 504 of base pad forming material having a working side 506 and an opposite side 508, a second supply roll 510 supplying a web 512 of impervious barrier layer forming material, and a third supply roll 514 supplying a web 516 of handle-forming material. As discussed hereinabove, the webs 504, 512 and 516 may be of various materials for the three respective layers of the multilayer pads produced.

Figure 26:
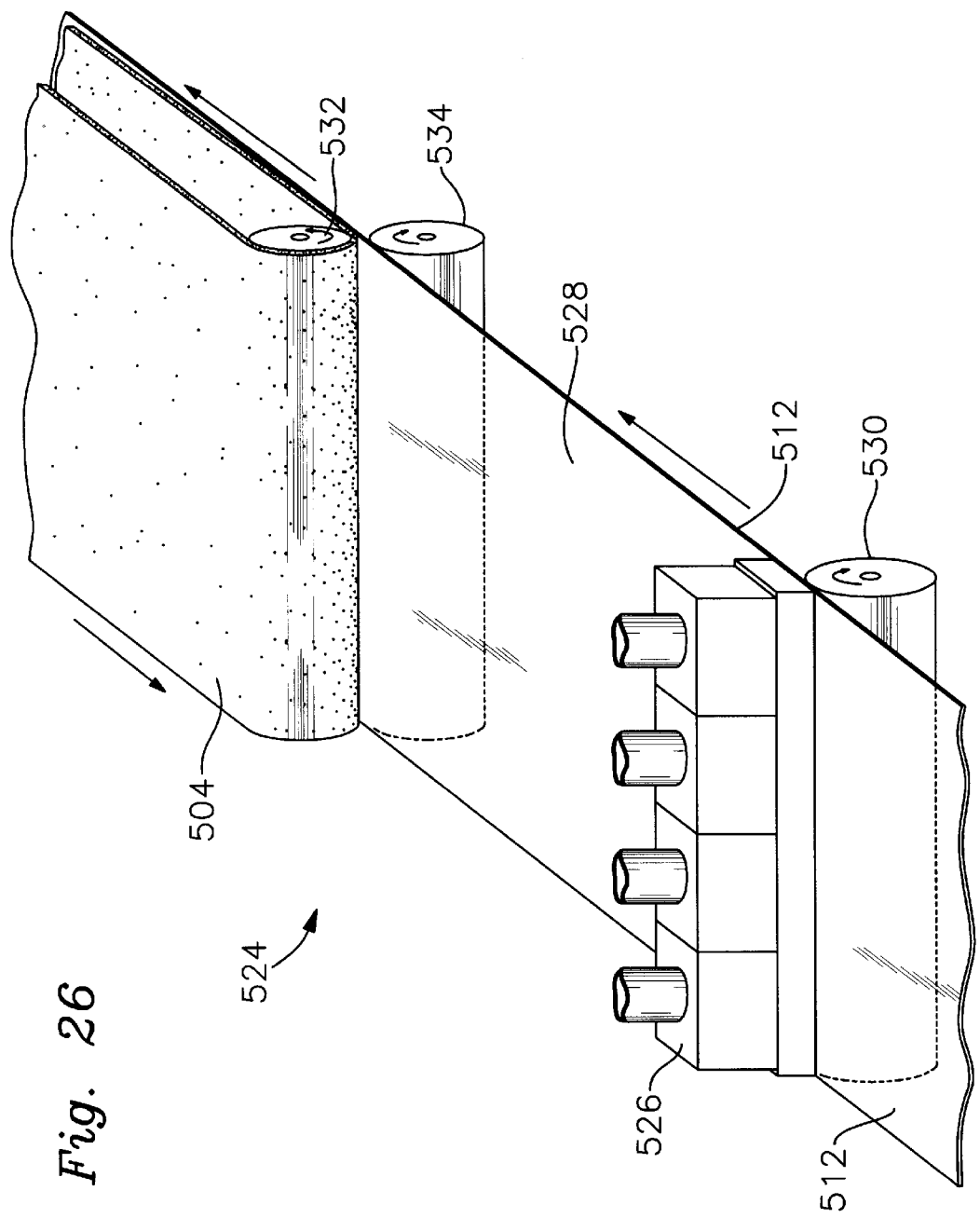
FIG. 26 is a three-dimensional enlarged representation of the full-width adhesive coating station in the machine of FIG. 25.

Referring to FIG. 26, as well as to FIG. 25, guide rollers 520 and 522 direct the base pad forming material web 504 to a full-width adhesive coating station 524. The full-width adhesive coating station 524 includes an adhesive applicator 526 which applies a uniform layer of suitable adhesive 528 onto the web 512, which travels over a chill roll 530. Hot-melt, solvent-based or water-based adhesive may be employed. Nip rollers 532 and 534 bring the web 504 of absorbent base pad forming material and the web 512 of barrier layer forming material together. Adhesive may be applied either to the web 504 of base pad forming material or to the web 512 of barrier layer material, but it is preferable to apply adhesive to the web 512 of barrier layer material.

Figure 27:
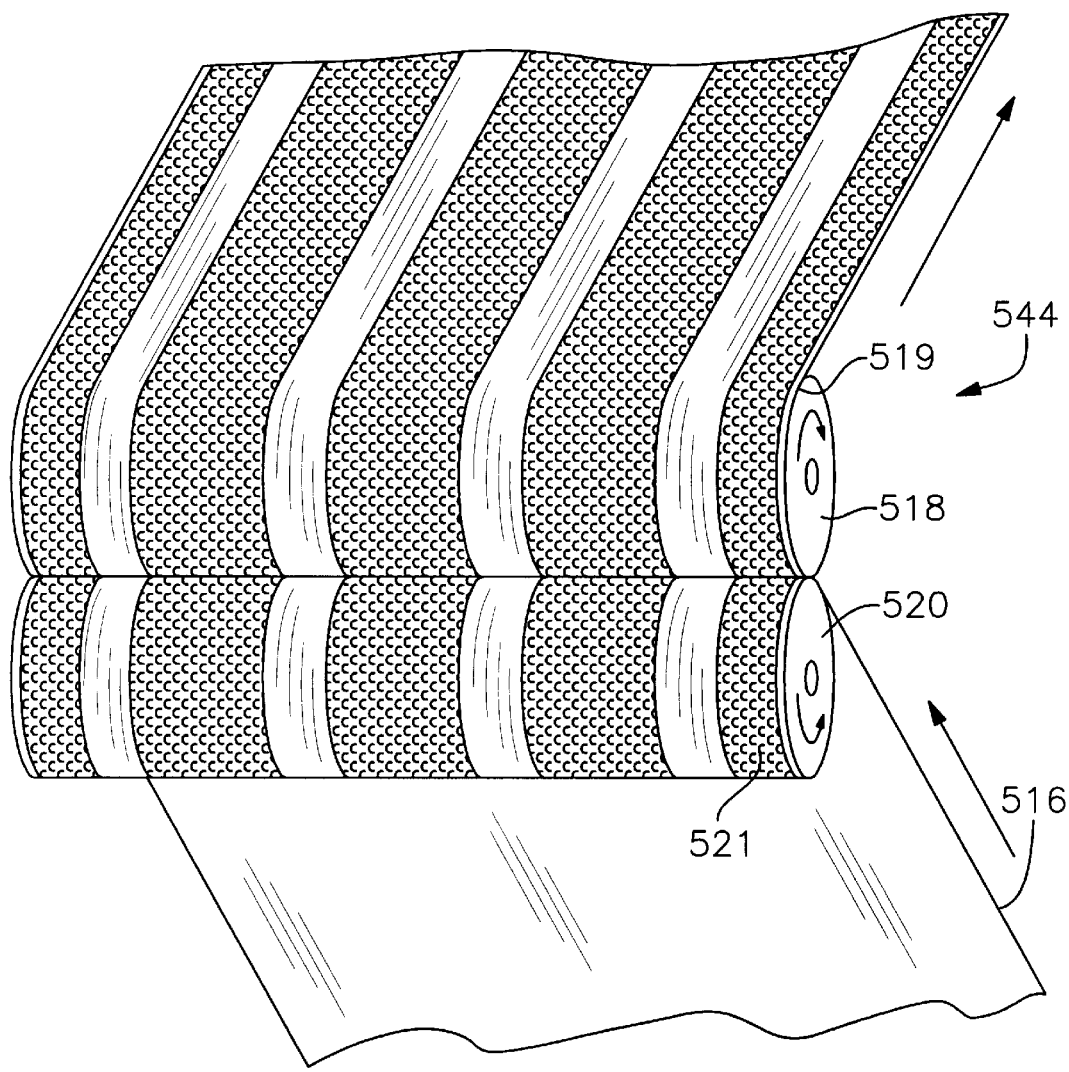
FIG. 27 is an enlarged three-dimensional representation of the embossing station in the machine of FIG. 25.

Referring to FIG. 27, as well as FIG. 25, the web 516 of handle-forming material is guided by representative guide roller 540 to an embossing station, generally designated 544. The embossing station 544 includes an embossing roller 518 patterned in zones 519 and an opposite nip roller 520, preferably with a corresponding pattern 521, that form embossed areas 524 on the web of handle material. The embossing roller 518 typically is not heated.

Figure 28:
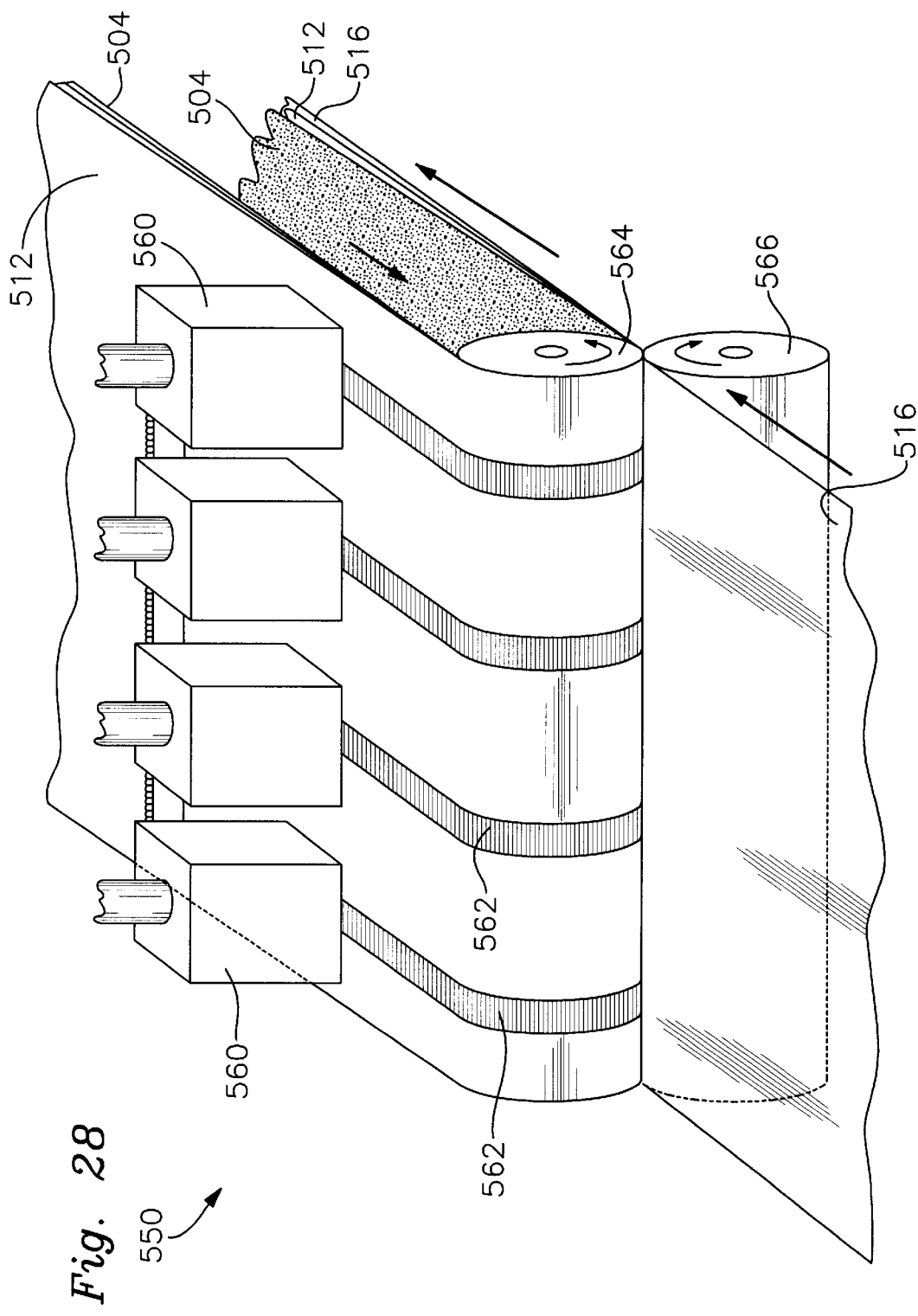
FIG. 28 is an enlarged representation of the adhesive zone coating station in the machine of FIG. 25.

Referring to FIG. 28, as well as FIG. 25, an adhesive zone coating station 550 is provided, into which the web 504 of absorbent base pad forming material with the joined web 512 of barrier forming material are guided together by means of guide rollers 552 and 554, as well as embossed handle forming material by guide roller 556.

The adhesive zone coating station 550 includes several slot nozzles 560 for applying adhesive in strips 562 to one or the other of the two webs being joined, defining the selective attachment areas of the ultimate pads. The slot nozzles 560 may be Series H200 Slot Nozzles, manufactured by Nordson Corporation of Duluth, Ga. The materials are pressed between a chill roll 564 and an opposing roller 566, with all three web layers joined together to form a multi-layer web at 568.

Figure 29:
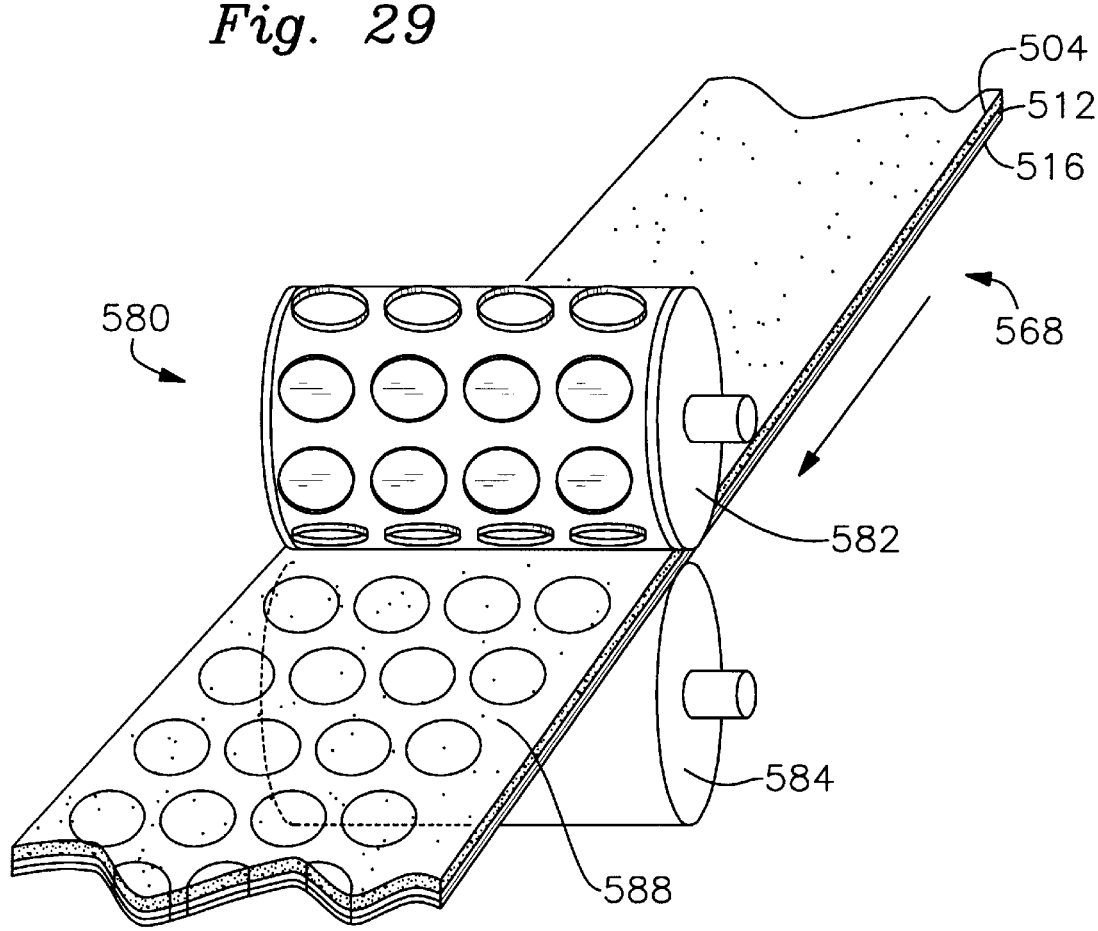
FIG. 29 is an enlarged representation of the die cutting die station in the machine of FIG. 25.

Referring to FIG. 29, as well as FIG. 25, the web 568 is guided by rollers 574 and 576 to a die cutting station 580. The die cutting station 580 includes an upper cutting die roll 582, and a lower anvil roll 584, which cooperate to cut through all three layers of the web 568, relative to the embossed areas and selective attachment areas as described hereinabove with reference to FIGS. 7, 13, 18 and 23.

In FIG. 29, individual pads 588 have been cut out, but are still retained within the multi-layer web. The web 568 travels across a flat plate (not shown), which prevents individual pads from prematurely falling out.

Figure 30:
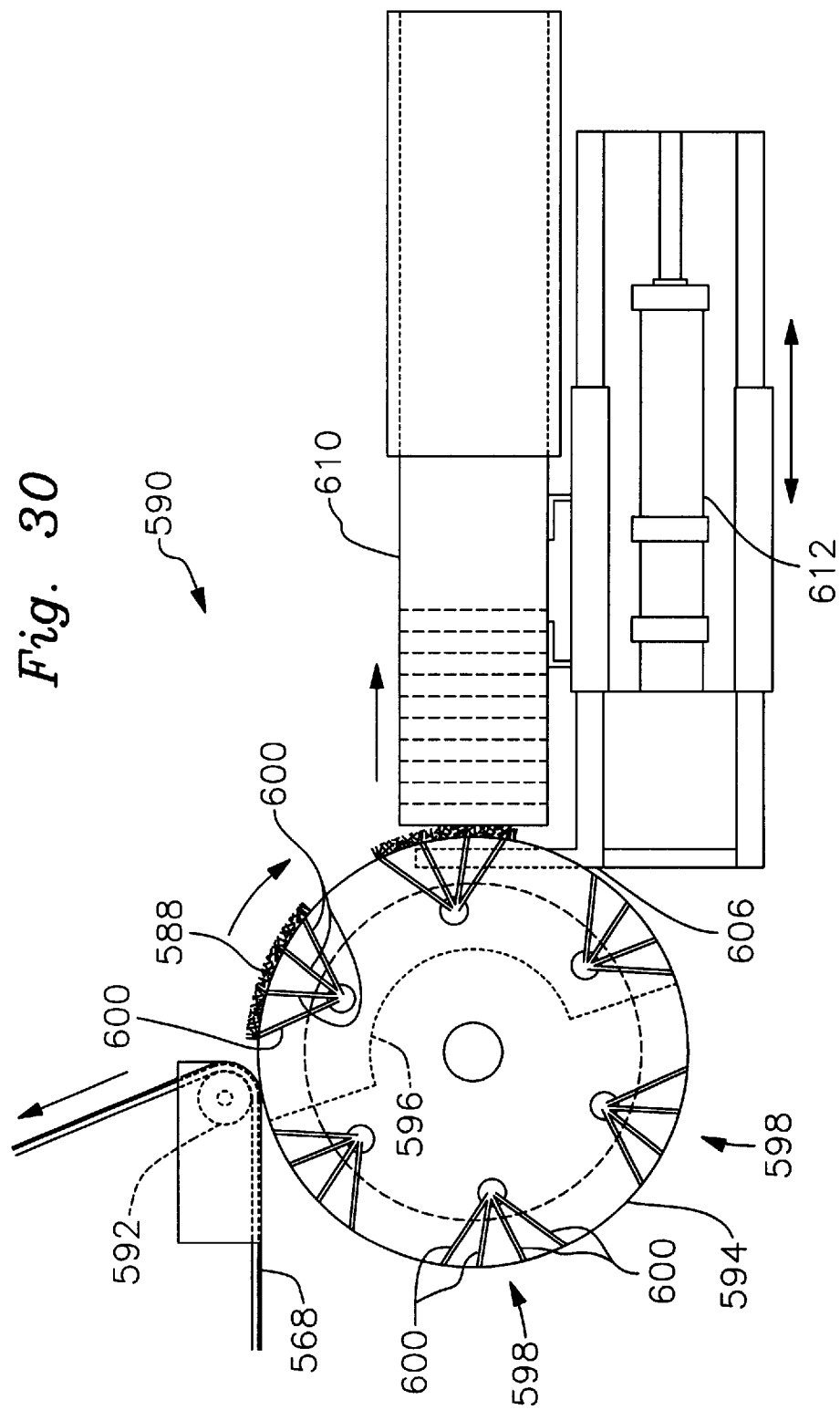
FIG. 30 is an enlarged the vacuum accumulation and stacking station in the machine of FIG. 25.
Figure 31:
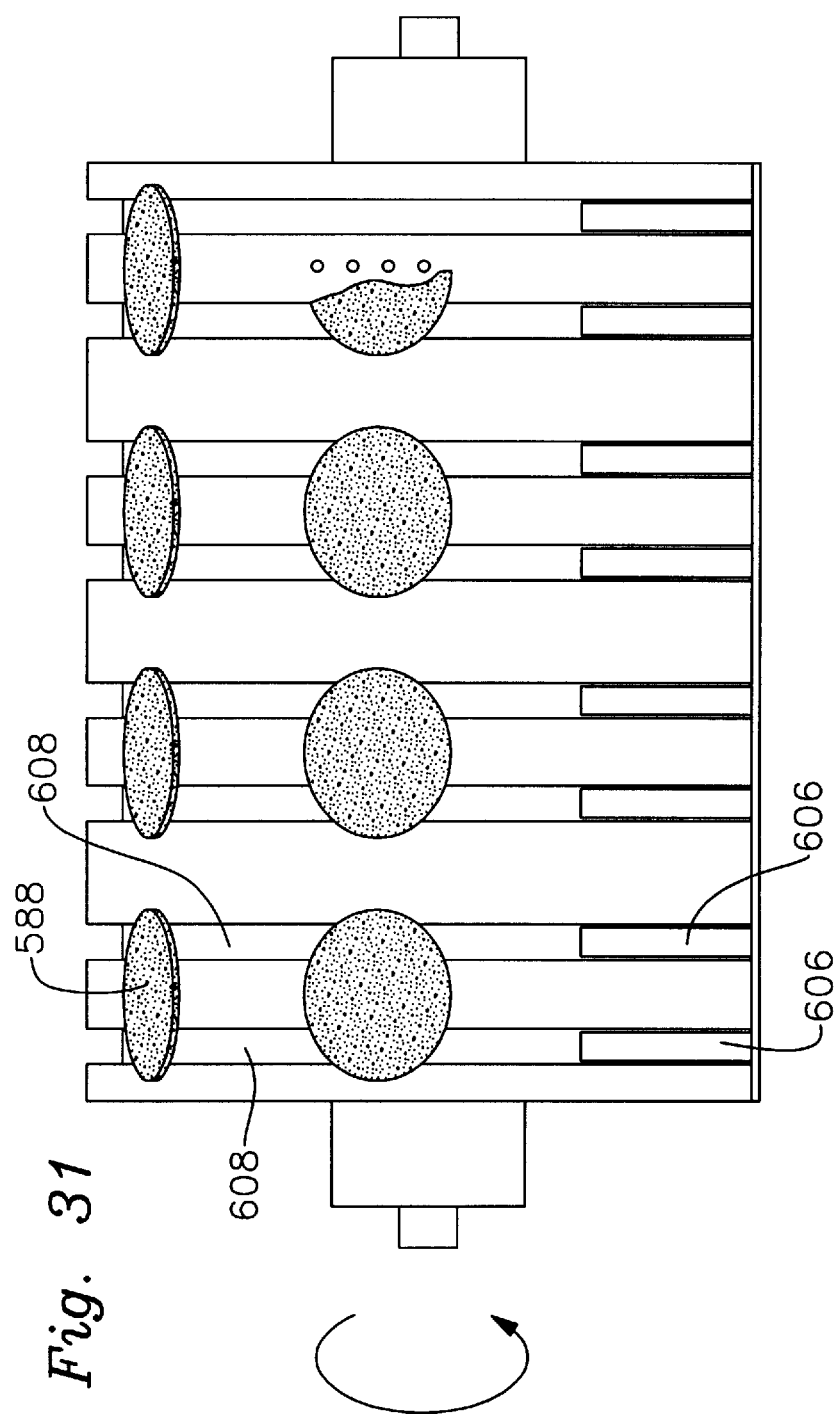
FIG. 31 is a front view of the pad accumulator of FIG. 30.

Referring next to FIGS. 30, 31 and 32, as well as to FIG. 25 the web 568, with pads 588 cut out but still retained by the web, enters a vacuum pad accumulator and stacking station 590.

Within accumulation and stacking station 590, the incoming web 568 encounters a sharp bend defined by a guide roller 592, which feeds into a rotating vacuum roll 594 including an internal vacuum manifold 596 and a plurality of pad-retaining sites 598, each defined by a set of four internal conduits 600 providing communication between the vacuum manifold 596 and the exterior surface of the roll 594 when a particular one of the sites 598 is rotated in position over the vacuum manifold 596. Thus, the individual pads 588 are delivered to the vacuum roll, handle-side down, and are temporarily retained via vacuum at the sites 598, as the sharp bend of guide roller 592 encourages the individual pads to become free of the web. A waste rewinder 604 collects the leftover web material 606, after the pads 588 have been detached.

As vacuum roll 594 rotates, pads 588 are individually carried to a near horizontal position, where stripper fingers 606 riding in grooves 608 of the vacuum roll 594 engage the pads (four across at a time in this particular embodiment), and pack the webs into stacking tubes 610. The stripper fingers 606 move towards and away from the stacking tubes 610 synchronized with the rotation of vacuum roll 594 as the pads 588 reach the stripping position, driven by an actuator cylinder 612. FIG. 32 also conceptually illustrates the manner in which product boxes 614 receive stacks of pads from the stacking tubes.

Figure 33:
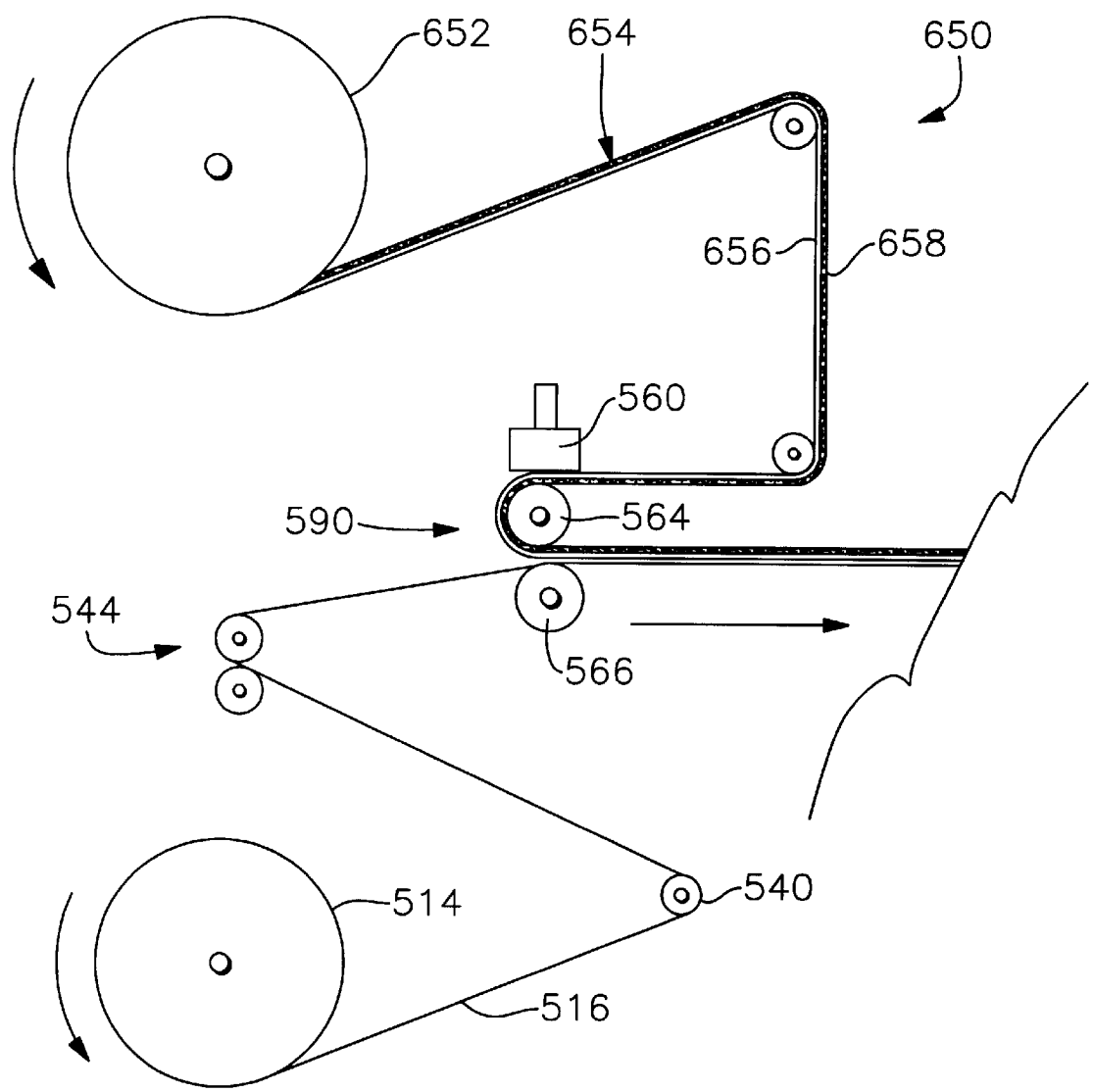
FIG. 33 is a schematic overview of a portion of a modified machine for producing multilayer pads.

Referring finally to FIG. 33, schematically depicted in overview is a portion 650 of a modified machine for manufacturing multilayer pads. The FIG. 33 machine 650 differs from the machine 500 of FIG. 25 in that, rather than the separate supply rolls 502 and 510 for supplying separate webs 504 and 512 of base pad and barrier material, a single supply roll 652 supplies a composite material web 654, including a layer 656 of impervious barrier forming material coated over a layer 658 of base pad forming material. The two layers 656 and 658 may be fused together, as described hereinabove with reference to FIG. 8. In FIG. 33, the full width adhesive coating station 524 of FIG. 25 is not used.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A multilayer pad comprising:
   an absorbent base pad having a working side, an opposite side, and an outer periphery;
   an impervious barrier layer having one side joined to said opposite side of said absorbent base pad, said barrier layer having an outer periphery coextensive with said outer periphery of said absorbent base pad; and
   a flexible handle having a central attached portion attached directly to the other side of said impervious barrier layer in a selective attachment area extending as a strip across said impervious barrier layer, and a pair of graspable portions on either side of said central attached portion, said handle having an outer periphery coextensive with said outer peripheries of said absorbent base pad and said impervious barrier layer when said graspable portions are lying adjacent to said impervious barrier layer.

2. A multilayer pad comprising:
   an absorbent base pad having a working side, an opposite side, and an outer periphery;
   an impervious barrier layer having one side joined to said opposite side of said absorbent base pad, said impervious barrier layer being coated over said absorbent base pad and said barrier layer having an outer periphery coextensive with said outer periphery of said absorbent base pad; and a flexible handle having a central attached portion attached to the other side of said impervious barrier layer in a selective attachment area extending as a strip across said impervious barrier layer, and a pair of graspable portions on either side of said central attached portion, said handle having an outer periphery coextensive with said outer peripheries of said absorbent base pad and said impervious barrier layer when said graspable portions are lying adjacent to said impervious barrier layer.

3. The multilayer pad of claim 2, wherein said impervious barrier layer is fused to said absorbent base pad.

4. The multilayer pad of claim 3, wherein said base pad comprises non-woven polypropylene fibers and said impervious barrier layer comprises polypropylene.

5. A multilayer pad comprising:

an absorbent base pad having a working side, an opposite side, and an outer periphery;

an impervious barrier layer having one side joined to said opposite side of said absorbent base pad, said barrier layer having an outer periphery coextensive with said outer periphery of said absorbent base pad; and a flexible handle having a central attached portion fused to the other side of said impervious barrier layer in a selective attachment area extending as a strip across said impervious barrier layer, and a pair of graspable portions on either side of said central attached portion, said handle having an outer periphery coextensive with said outer peripheries of said absorbent base pad and said impervious barrier layer when said graspable portions are lying adjacent to said impervious barrier layer.

6. The multilayer pad of claim 5, wherein said handle comprises polypropylene and said impervious barrier layer comprises polypropylene.

7. A multilayer pad comprising:

an absorbent base pad having a working side, an opposite side, and an outer periphery;

an impervious barrier layer having one side joined to said opposite side of said absorbent base pad by being coated over said absorbent base pad, said barrier layer having an outer periphery coextensive with said outer periphery of said absorbent base pad; and a flexible handle having an attached portion attached to the other side of said impervious barrier layer in a selective attachment area, and at least one graspable portion, said handle having an outer periphery coextensive with said outer peripheries of said absorbent base pad and said impervious barrier layer when said at least one graspable portion is lying adjacent to said impervious barrier layer.

8. The multilayer pad of claim 7, wherein said impervious barrier layer is fused to said absorbent base pad.

9. The multilayer pad of claim 8, wherein said base pad comprises non-woven polypropylene fibers and said impervious barrier layer comprises polypropylene.

10. A multilayer pad comprising:

an absorbent base pad having a working side, an opposite side, and an outer periphery;

an impervious barrier layer having one side joined to said opposite side of said absorbent base pad, said barrier layer having an outer periphery coextensive with said outer periphery of said absorbent base pad; and a flexible handle having an attached portion attached to the other side of said impervious barrier layer by fusing to said impervious barrier layer in a selective attachment area, and at least one graspable portion, said handle having an outer periphery coextensive with said outer peripheries of said absorbent base pad and said impervious barrier layer when said at least one graspable portion is lying adjacent to said impervious barrier layer.

11. The multilayer pad of claim 10, wherein said handle comprises polypropylene and said impervious barrier layer comprises polypropylene.

* * * * *